United States Patent [19]

Power et al.

[11] Patent Number: 5,531,221

[45] Date of Patent: Jul. 2, 1996

[54] DOUBLE AND SINGLE ACTING PISTON VENTILATORS

[75] Inventors: John S. Power; John J. O'Mahony, both of Galway, Ireland; Edwin B. Merrick, Stow, Mass.

[73] Assignee: Puritan Bennett Corporation, Carlsbad, Calif.

[21] Appl. No.: 304,046

[22] Filed: Sep. 12, 1994

[51] Int. Cl.[6] .................................................. A61M 16/00
[52] U.S. Cl. ........................... 128/205.18; 128/204.21; 128/204.18; 417/259
[58] Field of Search ..................... 128/204.18, 204.21, 128/205.18, 203.12, 204.25, 204.28, 205.13, 205.14, 205.15, 205.16, 205.17, 205.19; 417/259, 262, 242, 267, 315

[56] References Cited

U.S. PATENT DOCUMENTS

| | | | |
|---|---|---|---|
| 660,136 | 10/1900 | Welch | 417/259 |
| 961,000 | 7/1910 | Oddie | 417/259 |
| 1,344,994 | 6/1920 | Diserens | 417/259 |
| 1,488,171 | 3/1924 | Savidge | 417/259 X |
| 1,498,471 | 6/1924 | Miller | 417/259 |
| 2,408,765 | 10/1946 | Erickson | 417/259 |
| 3,599,633 | 8/1971 | Bessley | 128/205.18 |
| 3,729,000 | 4/1973 | Bell | 128/204.21 |
| 3,889,669 | 6/1975 | Weigl | 128/204.18 |
| 4,336,590 | 6/1982 | Jacq et al. | 128/204.21 X |
| 4,340,044 | 7/1982 | Levy et al. | 128/204.21 |
| 4,932,401 | 6/1990 | Perkins | 128/203.12 |
| 5,107,830 | 4/1992 | Younes | 128/204.18 |

FOREIGN PATENT DOCUMENTS

| | | | |
|---|---|---|---|
| 1319175 | 6/1993 | Canada. | |
| 1271902 | 7/1968 | Germany | 128/205.18 |
| 2-102383 | 4/1990 | Japan | 417/242 |
| 157638 | 10/1932 | Switzerland | 417/259 |
| 1555957 | 11/1979 | United Kingdom | 417/259 |

OTHER PUBLICATIONS

Younes, et al., "Proportional Assist Ventilation"; Am Rev Respir Dis 1992; 145: 121–129.
Younes, et al., "An apparatus for altering the mechanical load of the respiratory system", J. Appl. Physiol. .62(6): 2491–2499, 1987.

Primary Examiner—Edgar S. Burr
Assistant Examiner—Eric P. Raciti
Attorney, Agent, or Firm—Fulwider Patton Lee & Utecht

[57] ABSTRACT

The piston ventilators include a double acting reciprocating piston, in which the piston motion delivering breathing gas to a patient receiving assistance from the ventilator simultaneously draws in breathing gas from a source of breathing gas, and a single acting piston ventilator, in which only the delivery end of the cylinder is provided with inlet and exhaust valves. In the double acting piston ventilator, breathing gas is supplied to both ends of the piston cylinder through two intake valves, and exhausting breathing gas through two exhaust valves. Both intake valves of the cylinder are ducted to the breathing gas supply, and the two exhaust valves of the cylinder are ducted to a gas delivery limb of the ventilator connected to the patient's airway.

12 Claims, 3 Drawing Sheets

DOUBLE AND SINGLE ACTING PISTON VENTILATORS

BACKGROUND OF THE INVENTION

1. Field of the Invention

This invention relates generally to ventilators for delivering breathing gas to the lungs of a patient, and more particularly concerns a double acting reciprocating piston ventilator having a piston that is supplied with breathing gas on each stroke of the piston, automatically charging itself whenever breath support is delivered, and requiring no retraction time between breaths. A single acting piston is also disclosed that automatically draws breathing gas from a source only during delivery of breathing gas.

2. Description of Related Art

Medical ventilators are generally designed to ventilate a patient's lungs with breathing gas to assist a patient in breathing when the patient is somehow unable to adequately breath without assistance. Pressure assistance often can be instituted when the patient has already begun an inspiratory effort, typically by bellows or fixed volume piston type ventilators.

Conventional piston lung ventilators commonly use a single action piston, in which the gas to be delivered is drawn into a cylinder by the retraction of the piston and is subsequently delivered to the patient by advancing the piston. The supply flow rate during the retraction time of a single action piston can be much higher than the patient's peak flow demand. It would be desirable to provide a piston ventilator requiring a supply flow rate only as great as the rate required by the patient.

Such piston lung ventilators, while typically having piston seals, may allow small volumes of breathing gas with a high oxygen concentration to leak past the seals, to escape into the interior of the ventilator. A piston ventilator using an unsealed piston is also known that results in a higher volume of leakage. For example, in the known unsealed piston ventilator, the piston cylinder has a volume of about 2.7 liters, allowing for as much as 0.7 liters of compensation for leakage past the piston and volume lost due to the compressibility of the breathing gas in the cylinder and airway, while still maintaining the ability to deliver a breath of up to 2.0 liters inspired volume in one stroke of the piston. It is unsafe to allow high concentrations of oxygen to accumulate in the interior of an electrical product, due to the risk of fire, and it is therefore necessary with such single action ventilator systems to scavenge any gas mixture that has leaked past the piston outside the ventilator enclosure. The breathing gas mixture that remains in the piston to be delivered to the patient can also be diluted by the leakage, or "blow by" of room air that leaks past the piston during the time the piston is retracting, drawing breathing gas into the piston cylinder. It would be desirable to provide a piston ventilator in which any leakage of air past the piston to dilute the breathing gas mixture is avoided, and in which any leakage of the breathing gas mixture past the piston is retained within the piston cylinder, so that it does not need to be scavenged, and can be delivered to the patient.

In addition, since such single acting pistons have a fixed volume, in order for the ventilator to deliver a breath larger than the volume of the piston cylinder, the single acting piston must first advance, reverse direction, and then retract before advancing again, causing a significant interruption of flow in the time that is necessary for the single acting piston to cycle back to a "home" retracted position to deliver breath support to a patient. It would thus be desirable to provide a piston ventilator having a piston that automatically charges itself whenever breath support is delivered, and that can deliver a breath larger than the piston cylinder volume when required, without an appreciable interruption of flow, simply by reversing the direction of travel of the piston, by the use of multiple strokes of the piston, requiring no retraction time and a reversal time of only milliseconds between strokes of the piston to deliver breath support. A first embodiment of the present invention meets these needs, while a second embodiment of the invention provides gas scavenging and reduction of peak flow from the breathing gas supply.

SUMMARY OF THE INVENTION

Briefly, and in general terms, a first embodiment of the present invention provides for a ventilator system with a double acting reciprocating piston, in which the piston motion delivering breathing gas to a patient receiving assistance from the ventilator simultaneously draws in breathing gas from a source of breathing gas. This is accomplished by supplying breathing gas to both ends of the piston cylinder through two intake valves, and exhausting breathing gas through two exhaust valves. Both intake valves of the cylinder are ducted to the breathing gas supply, and the two exhaust valves of the cylinder are ducted to a gas delivery limb of the ventilator connected to the patient's airway. Breathing gas only needs to be supplied to the piston cylinder from the source of breathing gas at the rate required by the patient, and the problems of scavenging oxygenated breathing gas that has leaked past the piston and dilution of breathing gas by room air are eliminated. In the first preferred embodiment, volumes of breathing gas larger than the volume of the piston cylinder can also be delivered to the patient without interruption, allowing a ventilator incorporating the double acting piston to be constructed very compactly, such as would be suitable for use in emergency vehicles.

The first embodiment accordingly provides for a double acting piston ventilator system for providing breathing gas to a patient airway. The double acting piston ventilator system comprises a source of the breathing gas for providing a supply flow of the breathing gas, and a fixed volume piston cylinder having a reciprocating piston. Each end of the piston cylinder has an inlet valve connected to the source of breathing gas for receiving the flow of breathing gas, and each end has an outlet for delivering breathing gas to the airway.

The first embodiment of the invention also provides a method for supplying breathing gas to a patient airway from the ventilator system by providing a supply flow of the breathing gas to both ends of the piston cylinder, and actuating the piston to deliver a flow of the breathing gas from an end of the piston cylinder to the patient airway while simultaneously drawing the breathing gas into the other end of the piston cylinder. A preferred aspect of the method involves alternatingly actuating the piston to deliver a flow of the breathing gas from the first end of the piston cylinder while simultaneously drawing breathing gas into the second end of the piston cylinder, and actuating the piston to deliver a flow of the breathing gas from the second end of the piston cylinder while simultaneously drawing breathing gas into the first end of the piston cylinder.

In a second embodiment of the invention, only the delivery end of the cylinder is provided with inlet and exhaust valves. The inlet valve of the delivery end of the cylinder is connected to the other end of the cylinder, the reservoir end, having no associated valves. The exhaust valve of the delivery end of the cylinder is connected to the airway. The second embodiment of the invention provides for the containment and utilization of any breathing gas that leaks past the piston within the cylinder and requires a volume flow rate from the supply of breathing gas which is nearly equal to the volume flow rate which is delivered to the patient being ventilated.

These and other aspects and advantages of the invention will become apparent from the following detailed description, and the accompanying drawings, which illustrate by way of example the features of the invention.

DETAILED DESCRIPTION OF THE PREFERRED EMBODIMENTS

In single action piston ventilators, the supply flow rate during piston retraction can be much higher than the patient's peak flow demand. Single action piston ventilators may also allow oxygenated breathing gas to escape from the cylinder if it is not adequately sealed, necessitating additional equipment and safety precautions for scavenging the escaped breathing gas, and may also allow breathing gas being delivered to the patient to be diluted by room air. In addition, in delivering a volume of breathing gas larger than the volume of the piston cylinder, single acting pistons must first advance, reverse direction, and then retract before advancing again, causing a significant interruption of flow of breathing gas to the patient.

Figure 1:
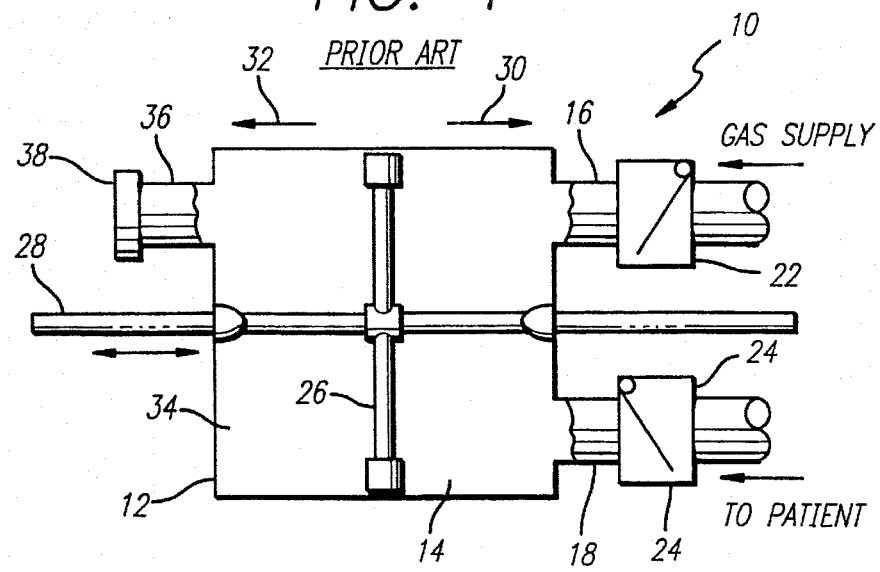
FIG. 1 is a diagram of a prior art piston ventilator.

As is illustrated in the FIG. 1, a typical prior art single action piston ventilator 10 includes a fixed volume piston cylinder 12 having a first gas delivery portion 14 with an inlet 16 for receiving mixed breathing gas and an outlet 18 for delivering the mixed breathing gas to the patient airway 20 during an inspiratory portion of a breath cycle. The inlet includes a check valve 22 allowing one way flow of the mixed gas into the piston cylinder, and the outlet 18 similarly has a check valve 24 allowing one way flow of the mixed gas to the patient airway. A reciprocating piston 26, mounted to a piston rod 28 for moving the piston, is disposed within the piston cylinder, and is movable within the piston cylinder between an extended position 30 in the first gas delivery portion 14 of the piston cylinder and a retracted position 32 in a second portion 34 of the piston cylinder on the opposite side of the piston from first gas delivery portion 14 of the piston cylinder. The second portion 34 of the piston cylinder includes a vent 36, typically with a filter 38, open to the atmosphere, through which leaked breathing gas can escape and room air can enter the piston cylinder.

Figure 2:
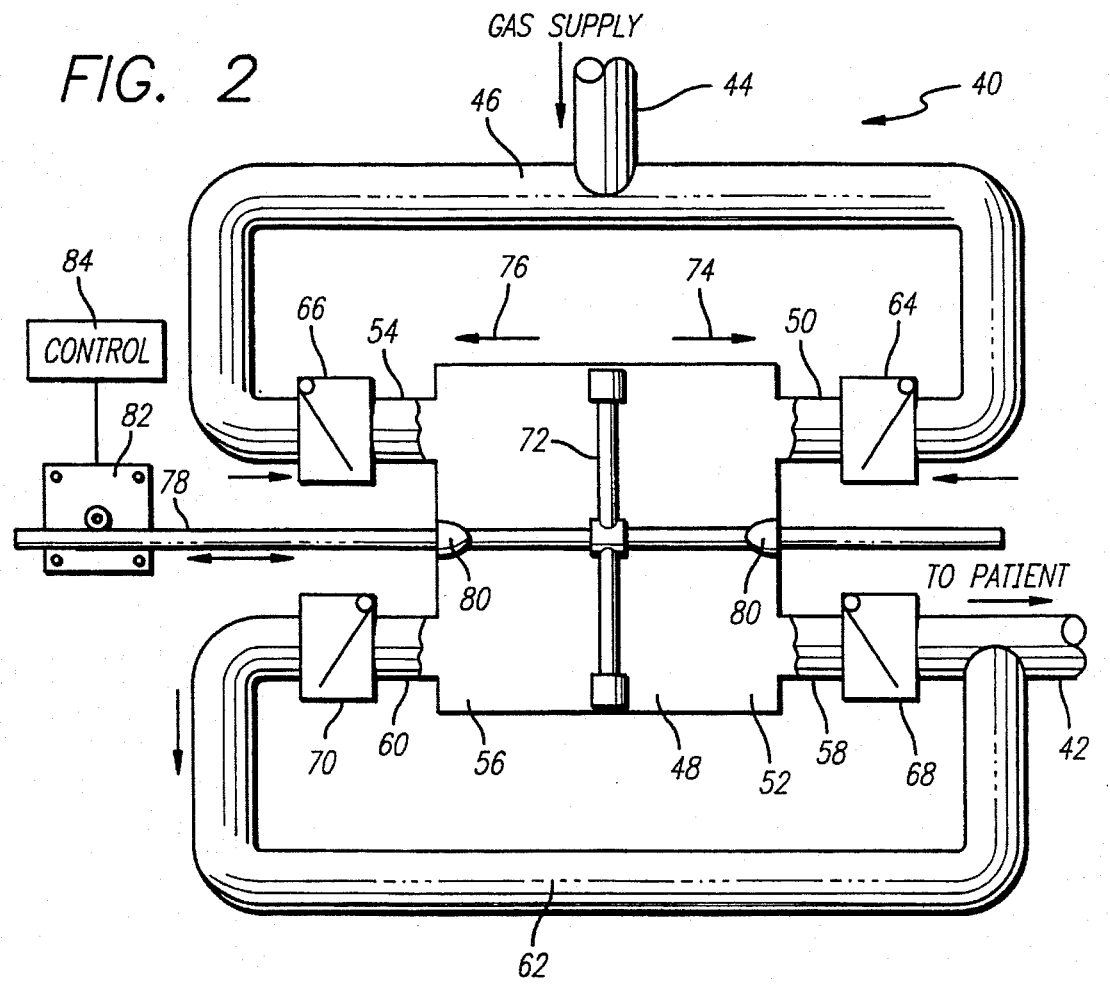
FIG. 2 is a diagram of a first embodiment of the piston ventilator of the invention.

With reference to FIG. 2, in a first embodiment the invention comprises a double acting piston ventilator 40 for providing breathing gas to a patient airway 42. A supply flow of breathing gas is provided to the double acting piston ventilator from a source of the breathing gas 44 through supply flow ducting 46 connected for fluid communication with a fixed volume piston cylinder 48. The piston cylinder has a first inlet 50 connected to the supply flow ducting at a delivery end 52 of the piston cylinder, and a second inlet 54 connected to the supply flow ducting at the other end 56 of the piston cylinder, for receiving the supply flow of breathing gas. Two outlets are provided in the piston cylinder for delivering mixed gas to the patient airway. As is illustrated in FIG. 2, a first outlet 58 is connected to the delivery end of the piston cylinder, and a second outlet 60 is connected to the second end of the piston cylinder, with each of the outlets being connected through outlet ducting 62 to the patient airway.

Inlet valve means are also preferably provided in each cylinder inlet to control the flow of the breathing gas into the piston cylinder, and in the first preferred embodiment illustrated in FIG. 2, a first check valve 64 is provided in the first inlet, and a second check valve 66 is provided in the second inlet, to allow flow of the supply of breathing gas into the piston cylinder through the inlets and to prevent backflow out of the piston cylinder through the inlets. Outlet valve means are also preferably provided in the outlet path to the patient airway to control the flow of the breathing gas from the piston cylinder to the patient airway. A first check valve 68 is provided in the first outlet, and a second check valve 70 is provided in the second outlet, to allow flow of breathing gas to the patient airway and to prevent backflow from the patient airway to the piston cylinder through the outlets.

A reciprocating piston 72 is disposed within the piston cylinder, and is movable between a first position 74 and a second position 76 near the ends of the piston cylinder for delivering breathing gas to the patient airway through the outlets. The reciprocating piston is typically mounted to a piston rod 78, and linear bearings 80 are currently preferably provided for the piston rod to ride on at both ends of the piston cylinder. The piston rod is preferably connected to and driven by means for moving the piston between the first and second positions, such as a rack and pinion motor 82 controlled by a control unit 84 such as a microcontroller or microprocessor for controlling the pressure and/or flow of breathing gas supplied by the piston chamber to the patient airway, so as to end the stroke of the piston at a precise volume, or to control the pressure profile of breathing gas delivery, for example. In order to minimize friction, conventional seals are not used. The system is designed to provide a small gap between the piston rod and the bearing housing to limit the leakage to acceptable levels.

In the first preferred embodiment, the piston cylinder of the double acting piston ventilator can typically be reduced in volume to about a quarter of the volume of conventional piston ventilators, allowing for a much more compact ventilator design that can be made more easily portable, such as for use in emergency vehicles, as it is not necessary for the piston to cycle back to a "home" retracted position for delivery of breath support to the patient. A breath larger than the cylinder volume can be delivered without an interruption of flow, simply by reversing the direction of travel of the piston, by the use of multiple strokes of the piston. Since the piston requires no retraction time between breaths, and requires minimal reversal time on the order of 20–30 milliseconds, breathing gas can be delivered to the patient on demand, and without significant interruption.

In addition, when a volume of gas is expelled from one end of the cylinder, an equal volume of breathing gas is drawn into the other end of the piston cylinder, automatically charging itself whenever breath support is delivered, so that the gas supply flow only needs to be made available at the rate required by the patient. Any "blow by" breathing gas that leaks past the piston is retained within the piston cylinder and can be delivered to the patient. Dilution of breathing gas by room air leaking past the piston is prevented, allowing for delivery of up to 100% oxygen to the patient, since the correct mixture of breathing gas is provided on both sides of the piston, and additional dilution by room air is not possible.

Figure 3:
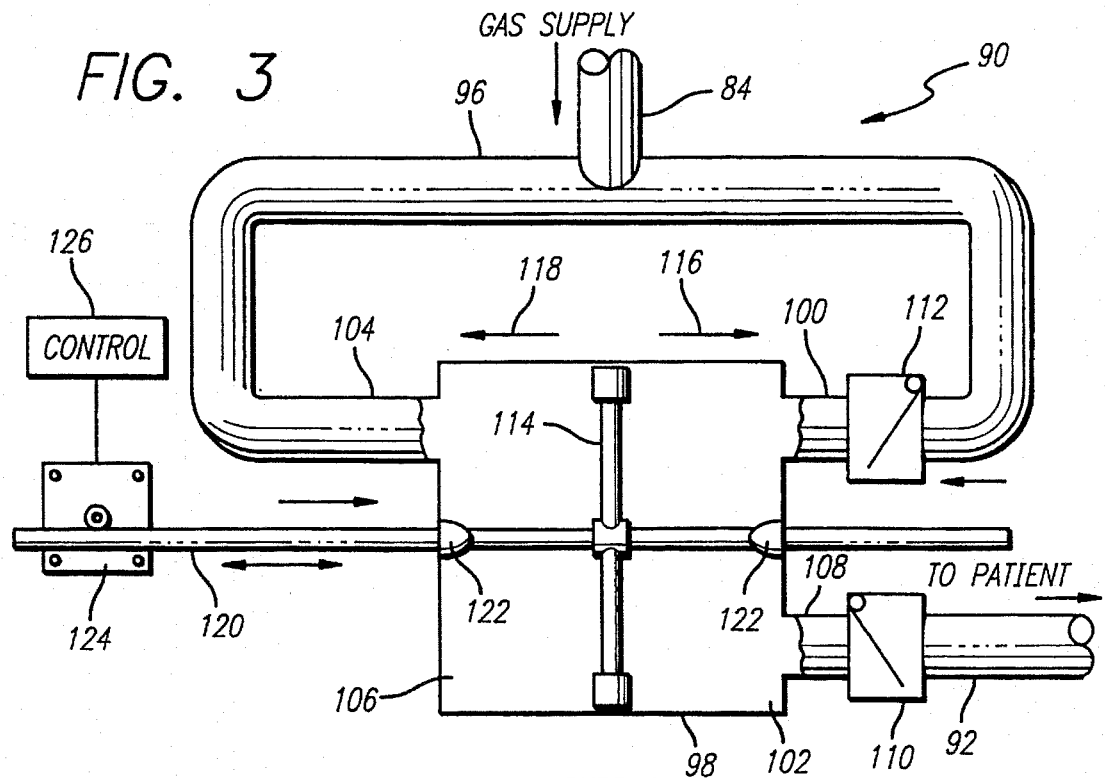
FIG. 3 is a diagram of a second embodiment of the piston ventilator of the invention.

In a second preferred embodiment illustrated in FIG. 3, the design of the piston ventilator can also be economized, by employing check valves at only one end of the piston cylinder, rather than providing two check valves to both ends of the cylinder. In this embodiment, a single acting piston ventilator 90 provides breathing gas to a patient airway 92, receiving a supply flow of breathing gas from a source 94 through supply flow ducting 96 connected for fluid communication with a fixed volume piston cylinder 98. The piston cylinder has a first inlet 100 connected to the supply flow ducting at a delivery end 102, and a second inlet 104 connected to the supply flow ducting at a reservoir end 106 of the piston cylinder. In this embodiment, however, only one outlet 108 is provided in the piston cylinder for delivering mixed gas to the patient airway, and is provided with a check valve 110 to allow flow of breathing gas to the patient airway and to prevent backflow from the patient airway to the piston cylinder through the outlet.

As is shown in FIG. 3, a check valve 112 is also provided in only the piston cylinder inlet located at the same side as the valved outlet, to control the flow of the breathing gas into the piston cylinder, so as to allow flow of the supply of breathing gas into the piston cylinder through the inlets and to prevent backflow out of the piston cylinder through the inlets while breathing gas is being delivered through the piston outlet to the patient airway. A reciprocating piston 114 is disposed within the piston cylinder, and is movable between a first position 116 and a second position 118 near the ends of the piston cylinder for delivering breathing gas to the patient airway through the outlets. As in the first embodiment, the reciprocating piston is typically mounted to a piston rod 120, and linear bearings 122 are also provided in the piston cylinder for the piston rod, at both ends of the piston cylinder. The piston rod is preferably driven by means for moving the piston between the first and second positions, such as a rack and pinion motor 124 controlled by a control unit 126 such as a microcontroller for controlling the pressure and/or flow of breathing gas supplied by the piston chamber to the patient airway.

In the second preferred embodiment, while the piston delivers breathing gas through the outlet check valve to the patient airway, the breathing gas mixture is simultaneously drawn into the piston cylinder through the inlet at the other end of the piston cylinder. During piston retraction, the supplied gas mixture is readily transferred through the gas supply flow duct from the end of the piston cylinder without a check valve to the delivery end of the piston cylinder. While breathing gas is not delivered to the patient's airway with both strokes of the piston, breathing gas is required to be delivered to the cylinder only during breathing gas delivery to the patient and only at a flow rate near the flow rate delivered to the patient. In addition, since no vent to the atmosphere is required by this design, gas leaking past the piston does not need to be scavenged, and can be delivered to the patient. Room air is also not permitted to leak past the piston to dilute the gas mixture, so that up to 100% oxygen can be delivered when needed, without dilution.

Figure 4:
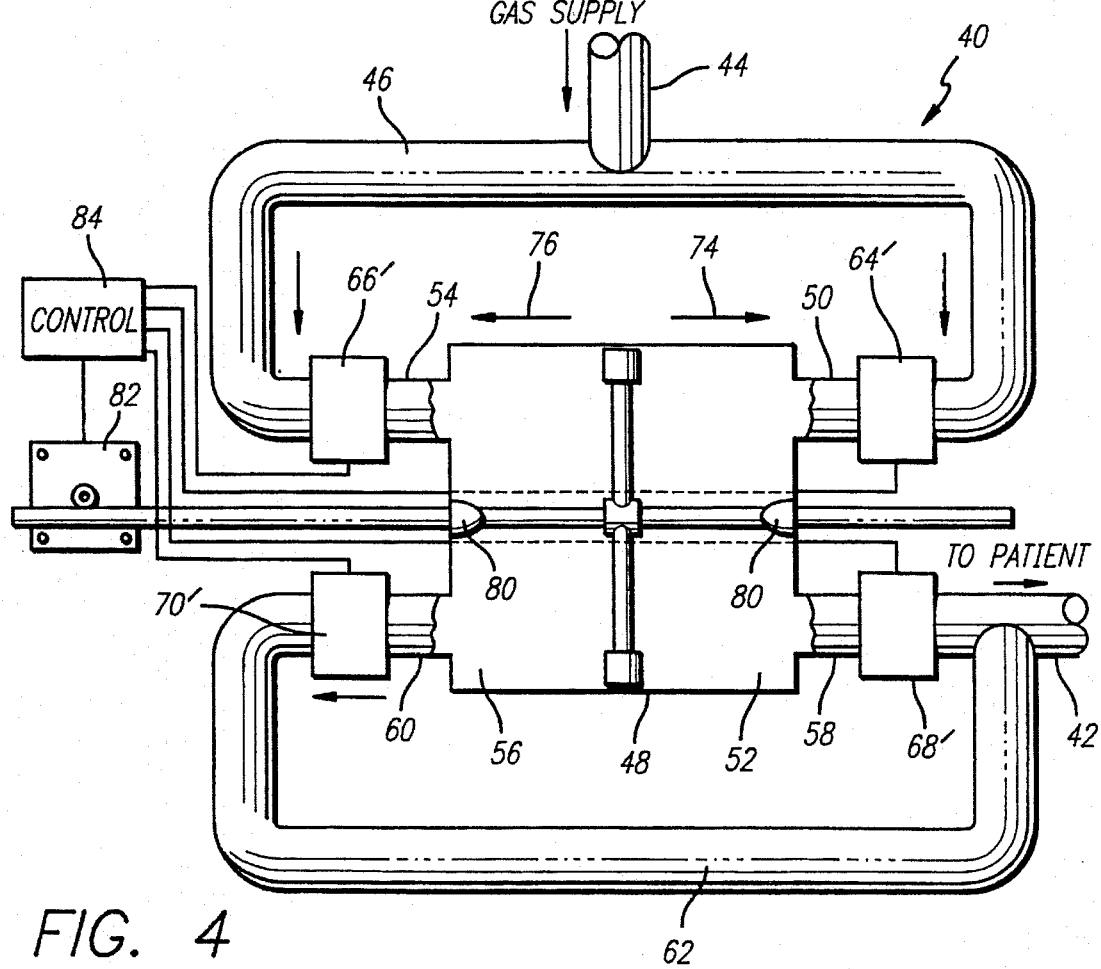
FIG. 4 shows an alternate embodiment of the piston ventilator of the invention similar to that of FIG. 2.
Figure 5:
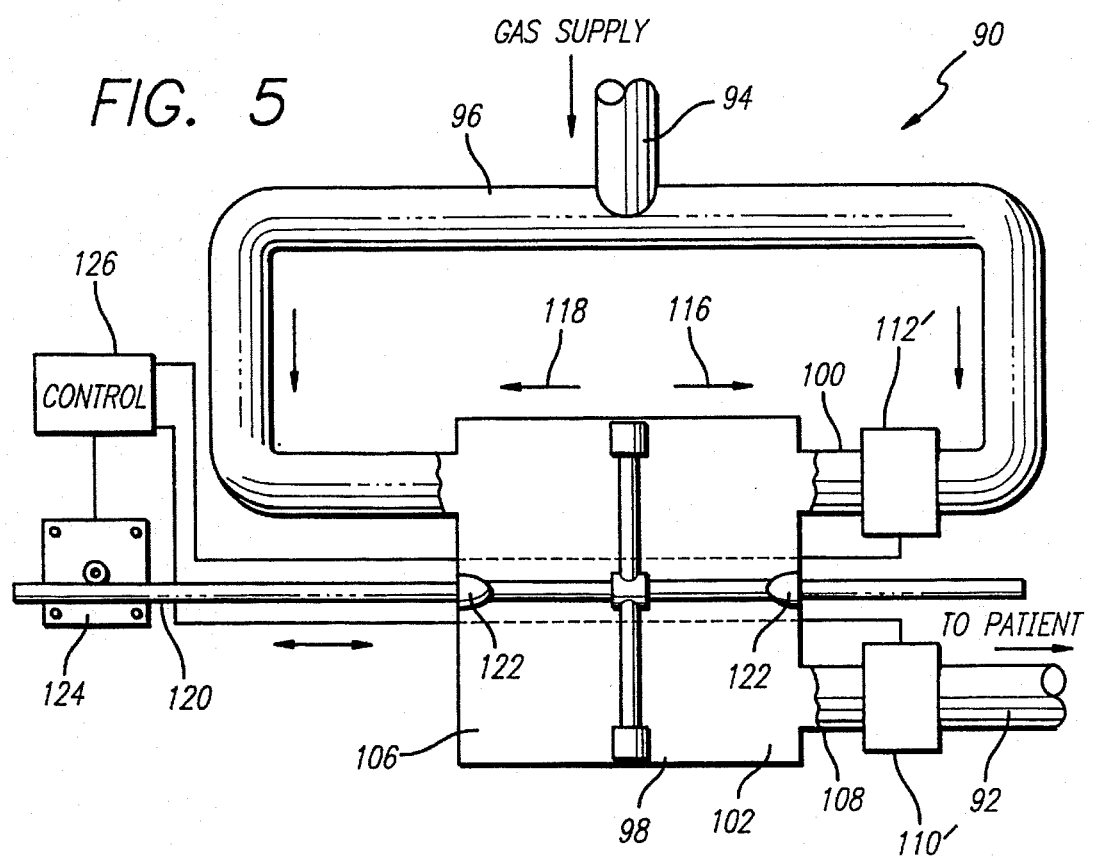
FIG. 5 shows an alternate embodiment of the piston ventilator of the invention similar to that of FIG. 4.

It should be recognized that the passive check valves in the ventilator system can also be replaced by actively controlled valves. Thus, the check valves 64, 66, 68 and 70 of FIG. 2 can be replaced by actively controlled valves 64', 66', 68' and 70', such as solenoid valves or pneumatically actuated valves connected to and controlled by the control unit 84, as is illustrated in FIG. 4. Similarly, as is shown in FIG. 5, actively controlled valves 110' and 112', such as solenoid valves or pneumatically actuated valves connected to and controlled by the control unit 126, can be substituted for the check valves 110 and 112 of FIG. 3.

In operation, as the piston travels in a direction so as to compress the breathing gas contained in the delivery end of the cylinder, breathing gas passes through the exhaust valve into the airway. Simultaneously, breathing gas is drawn from the supply of breathing gas into the reservoir side of the cylinder, which is caused to expand in volume, by an amount nearly equal to the volume expelled through the exhaust valve by the piston. Thus the flow rate into the reservoir end of the cylinder is nearly equal to the flow rate of the breathing gas expelled through the exhaust valve from the delivery end of the cylinder. At the end of the patient's inspiration, the piston is caused to move in a direction such as to compress the breathing gas contained in the reservoir end of the cylinder. This constitutes the second stroke of the piston. During the second stroke of the piston, breathing gas is transferred from the reservoir end of the cylinder, through the inlet valve of the delivery end of the cylinder, into the delivery end of the cylinder. During the second stroke of the piston no appreciable flow from the source of breathing gas occurs, and there may in fact be a small reverse flow equal to the expansion of the gas remaining in the delivery end of the cylinder as it returns to a pressure equal to the breathing gas supply pressure.

In both methods of the invention for supplying breathing gas to a patient airway from a ventilator system as described above, a supply flow of the breathing gas is provided to at least one of the first and second ends of the piston cylinder, and the piston is actuated to deliver a flow of the breathing gas from at least one of the first and second ends of the piston cylinder to the patient airway, while simultaneously drawing the breathing gas into the other of the first and second ends of the piston cylinder. In the embodiment of FIG. 2, the piston can be alternatingly actuated in one direction to deliver a flow of the breathing gas from the first end of the piston cylinder while simultaneously drawing breathing gas into the second end of the piston cylinder, and then actuated in the opposite direction to deliver a flow of the breathing gas from the second end of the piston cylinder while simultaneously drawing the breathing gas into the first end of the piston cylinder.

It has thus been demonstrated that the apparatus and methods of the invention provide for a double acting piston ventilator and a single acting piston ventilator in which breathing gas is supplied to the cylinder at a flow rate limited to near the patient's required flow of breathing gas. The problem of containment and utilization of breathing gas leaked past the piston is eliminated. The construction of the double acting piston ventilator allows the piston motion to simultaneously draw breathing gas from the source of breathing gas, and to deliver breathing gas to the patient airway. In one preferred embodiment, volumes of breathing gas larger than the volume of the piston cylinder can be delivered to the patient without interruption.

Figure 6:
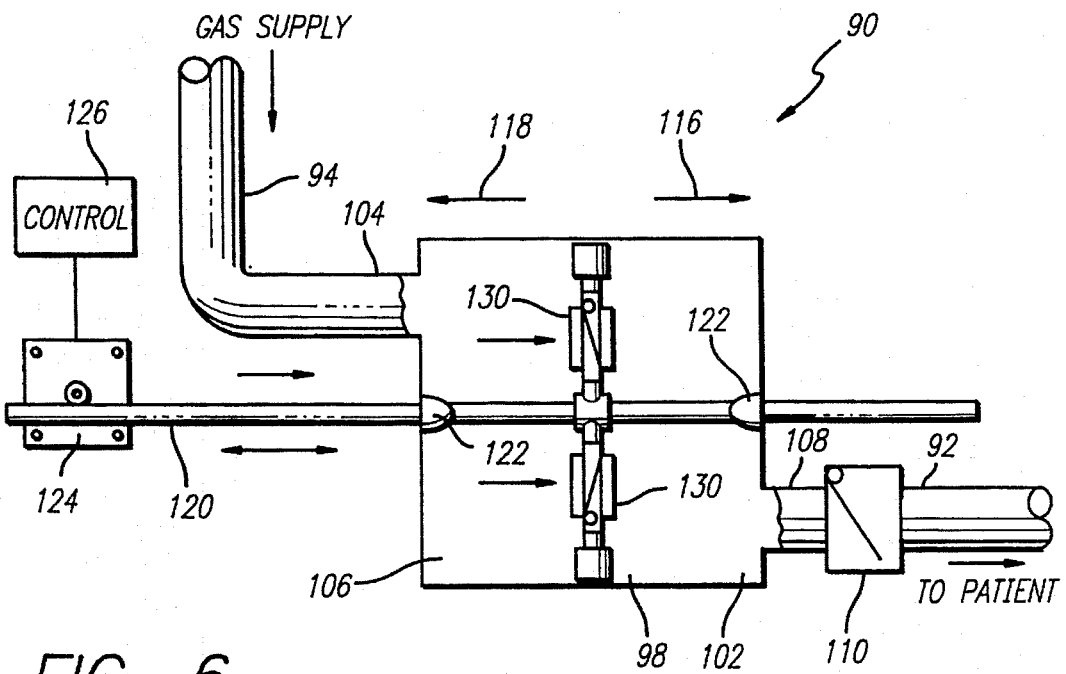
FIG. 6 shows another alternate embodiment similar to that of FIG. 5 with a transfer valve disposed in the piston.

It should be apparent that various alternate configurations of the embodiments of the piston ventilator of the invention are possible. For example, as is illustrated in FIG. 6, in a variation of the second embodiment, one or more one-way transfer valves 130 could also be mounted in the piston itself, to provide for the gradual filling of one side of the cylinder while the other side is delivering flow, followed by rapid retraction not limited by the flow rate of the breathing gas supply. In addition, the piston can be sealed or unsealed, and a single bearing can be provided at one end of the piston rod. The control unit can also comprise an analog circuit instead of a microprocessor.

It will thus be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A single acting piston ventilator system for providing breathing gas to a patient airway, comprising:

a source of said breathing gas for providing a supply flow of said breathing gas;

a fixed volume piston cylinder having a first end and a second end, a first inlet connecting said first end of said piston cylinder in fluid communication with said source of breathing gas for receiving said supply flow of breathing gas, a second inlet connecting said second end of said piston cylinder in fluid communication with said source of breathing gas for receiving said supply flow of breathing gas, said first and second inlets being connected in fluid communication, and an outlet connected to said first end of said piston cylinder for delivering mixed gas to the patient airway;

a single inlet valve, said inlet valve located in said first inlet for allowing flow of said mixed gas into said piston cylinder;

outlet valve means in said outlet for allowing a flow of said mixed gas to the patient airway;

a reciprocating piston disposed within said piston cylinder and moveable between said first and second ends of said piston cylinder; and means for moving said piston between said first and second ends.

2. The piston ventilator system of claim 1, further including control means for controlling said means for moving said piston for controlling pressure and flow of breathing gas supplied by the piston cylinder to the patient airway.

3. The piston ventilator system of claim 2, wherein said single inlet valve comprises an actively controlled valve controlled by said control means.

4. The piston ventilator system of claim 1, wherein said single inlet valve comprises a check valve.

5. The piston ventilator system of claim 1, wherein said outlet valve means comprises a check valve.

6. The piston ventilator system of claim 2, wherein said outlet valve means comprises an actively controlled valve connected to and controlled by said control means.

7. A single acting piston ventilator system for providing breathing gas to a patient airway, consisting essentially of:

a source of said breathing gas for providing a supply flow of said breathing gas;

a fixed volume piston cylinder having a first end and a second end, a first inlet connecting said first end of said piston cylinder in fluid communication with said source of breathing gas for receiving said supply flow of breathing gas, a second inlet connecting said second end of said piston cylinder in fluid communication with said source of breathing gas for receiving said supply flow of breathing gas, said first and second inlets being connected in fluid communication, and an outlet connected to said first end of said piston cylinder for delivering mixed gas to the patient airway;

inlet valve means in said first inlet for allowing flow of said mixed gas into said piston cylinder;

outlet valve means in said outlet for allowing a flow of said mixed gas to the patient airway;

a reciprocating piston disposed within said piston cylinder and moveable between said first and second ends of said piston cylinder; and means for moving said piston between said first and second ends.

8. The piston ventilator system of claim 7, wherein said inlet valve means comprises a check valve.

9. The piston ventilator system of claim 7, wherein said outlet valve means comprises a check valve.

10. A single acting piston ventilator system for providing breathing gas to a patient airway, consisting essentially of:

a source of said breathing gas for providing a supply flow of said breathing gas;

a fixed volume piston cylinder having a first end and a second end, a first inlet connecting said first end of said piston cylinder in fluid communication with said source of breathing gas for receiving said supply flow of breathing gas, a second inlet connecting said second end of said piston cylinder in fluid communication with said source of breathing gas for receiving said supply flow of breathing gas, said first and second inlets being connected in fluid communication, and an outlet connected to said first end of said piston cylinder for delivering mixed gas to the patient airway;

inlet valve means in said first inlet for allowing flow of said mixed gas into said piston cylinder;

outlet valve means in said outlet for allowing a flow of said mixed gas to the patient airway;

a reciprocating piston disposed within said piston cylinder and moveable between said first and second ends of said piston cylinder;

means for moving said piston between said first and second ends; and control means for controlling said means for moving said piston for controlling pressure and flow of breathing gas supplied by the piston cylinder to the patient airway.

11. The piston ventilator system of claim 10, wherein said inlet valve means comprises an actively controlled valve controlled by said control means.

12. The piston ventilator system of claim 10, wherein said outlet valve means comprises an actively controlled valve connected to and controlled by said control means.

* * * * *